Figure 1:
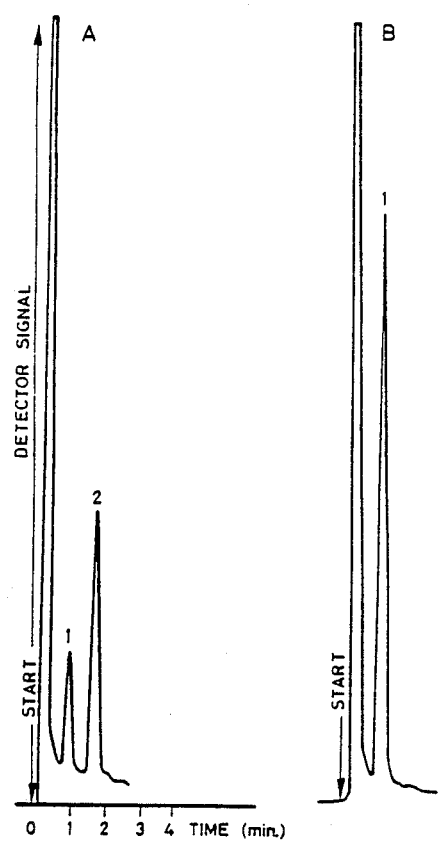

United States Patent [19]

Knausz et al.

[11] Patent Number: 4,831,173

[45] Date of Patent: May 16, 1989

[54] TRIMETHYLSILYLCARBAMATES AND A PROCESS FOR THE PREPARATION THEREOF

[75] Inventors: Dezö Knausz; Béla Csákvári; István Gebhardt; Aranka Meszticzky; Zsuzsanna Kolos; János Rohonczy; Ferenc Szederkényi; Kálmán Ujszászy; János Volford, all of Budapest, Hungary

[73] Assignee: Eotvos Lorand Tudomanyegyetem, Budapest, Hungary

[21] Appl. No.: 909,127

[22] Filed: Sep. 18, 1986

[30] Foreign Application Priority Data

Nov. 1, 1985 [HU] Hungary ............................ 4185/85

[51] Int. Cl.[4] ............................................. C07F 7/10
[52] U.S. Cl. ................................................. 556/420
[58] Field of Search ..................................... 556/420

[56] References Cited

U.S. PATENT DOCUMENTS 3,816,359  6/1974  Creamer ..................... 556/420 X
4,631,346 12/1986  Webb et al. ................. 556/420

Primary Examiner—Paul F. Shaver
Attorney, Agent, or Firm—Herbert Dubno; Jonathan Myers

[57] ABSTRACT

The invention relates to new compounds of the general formulae (I) and/or (II),

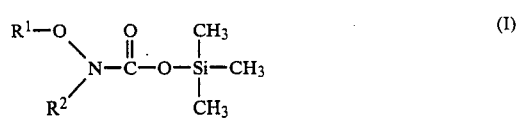

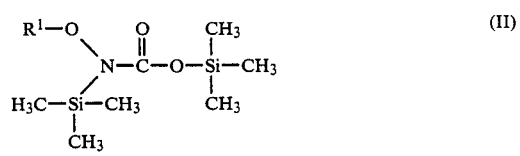

wherein
$R^1$ is a $C_{1-6}$ alkyl or an aralkyl group, and
$R^2$ is hydrogen or a $C_{1-6}$ alkyl group.

According to another aspect of the invention there are provided processes for the preparation of these compounds.

The compounds of the general formulae (I) and/or (II) are utilizable for the oxymation and/or trimethylsilylation of any substrate bearing an oxo group and/or a silylable polar hydrogen.

The compounds of the general formula (VI):

$$(CH_3)_3Si-Y-Z=N-OR^1 \quad (VI)$$

wherein
$R^1$ is as defined above
Y is oxygen, nitrogen or sulphur atom or a carboxylate anion, and
Z is the skeleton of the substrate, said compounds being formed in the oxymation and/or trimethylsilylation reaction, are also within the scope of the invention.

4 Claims, 1 Drawing Sheet

TRIMETHYLSILYLCARBAMATES AND A PROCESS FOR THE PREPARATION THEREOF

The invention relates to new N-substituted carbamic acid trimethylsilyl esters of the formulae (I) and/or (II),

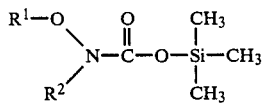

(I)

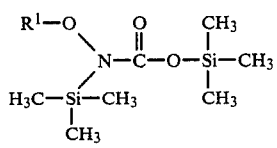

(II)

wherein
$R^1$ stands for a $C_{1-6}$ alkyl or aralkyl group, and
$R^2$ is hydrogen or a $C_{1-6}$ alkyl group.

The invention also provides a process for the preparation of the new compounds.

Silylcarbamates have been synthesized in several different ways. One of them is disclosed in Dutch Pat. No. 258,303, teaching that certain silylamines by addition of carbon dioxide form the corresponding silylcarbamates. A serious disadvantage of this process is that the starting silylamines can only be prepared with poor yields by conventional silylation techniques. Another process is described in Zh. Obshch. Khim, 46(12), 2712 (1976) whereby certain amines with hexamethyldisilazane and carbon dioxide give the corresponding silylcarbamates. Here the need for an extra reagent, i.e. hexamethyldisilazane and the low yields by which it is obtained from trimethylchlorosilane are the drawbacks of the process. According to DE-OS No. 2,722,117 first an amine is reacted with carbon dioxide to give the corresponding alkylammonium salt of the carbamic acid which is then silylated with trimethylchlorosilane. An improved version of this process is described in the Hungarian Patent No. 185,931 whereby a chlorinated hydrocarbon is applied as reaction medium resulting in relatively higher yields, shorter reaction time and improved purity of the product. However, in both methods only one half of the amine used is utilized at best for the synthesis of the desired compound, while the other half of it forms alkylammonium chloride. This is again, a serious drawback particularly when expensive alkyloxyamines or aralkyloxy amines are used.

It was therefore our object to synthesize reactive silyl derivatives with good yields in terms of the starting substances utilized and to provide a process with simpler and/or less steps for the preparation of the desired compounds.

It has been found that the new compounds of the formulae (I) and/or (II), wherein $R_1$ and $R_2$ have the same meaning as given above, are highly reactive and can be widely utilized primarily for silylation or for oximation. What is more, under certain conditions both derivatives can be formed simultaneously.

It has further been found that the new compounds of the formulae (I) and/or (II) can be prepared from amine of the formula (III),

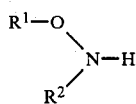

(III)

wherein $R^1$ and $R^2$ have the same meanings as given for the formula (I), or from an acid addition salt, preferably a hydrochloride thereof.

More particularly, when the process starts from an amine of the formula (III) or an acid addition salt thereof, wherein $R^2$ is hydrogen and $R^1$ is as defined above, a mixture of the respective products of the formulae (I) and (II) are formed. Under heating the product of the formula (I) undergoes autosilylation yielding the corresponding product of the formula (II). When the process starts from an amine of the formula (III) or an acid addition salt thereof, wherein $R^2$ is a $C_{1-6}$ alkyl group and $R^1$ is as defined above, the respective compound of the formula (I) is obtained as a sole product.

According to the invention there is provided a process for the preparation of new compounds of the formulae (I) and/or (II), wherein
$R^1$ is a $C_{1-6}$ alkyl or an aralkyl group, and
$R^2$ is hydrogen or a $C_{1-6}$ alkyl group,
in which
(a) when compounds of the formulae (I) and (II) are to be obtained
(1) a mole of an amine of the formula (III), wherein $R^1$ has the same meaning as defined above and $R^2$ is hydrogen, or an acid addition salt thereof, is reacted with carbon dioxide in an organic solvent along with 1–5 moles, preferably 1–4 moles of a tertiary amine, preferably of a tri($C_{1-6}$alkyl)amine, at a temperature ranging from 0° C. to the boiling point of the reaction mixture, to form the respective N-substituted tertiary ammonium carbamate of the formula (IV),

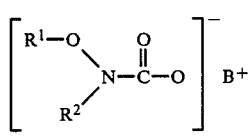

(IV)

wherein $R^1$ and $R^2$ have the same meanings as defined above and $B^+$ stands for a tertiary ammonium ion, preferably a tri($C_{1-6}$alkyl)ammonium ion,
(2) to the reaction mixture containing a mole of said compound, 0.5–5.0 moles, preferably 2–3 moles of trimethylsilylating agent is added to yield the desired compounds, or if desired steps (1) and (2) are combined into a one-step process, and in either case
(3) the salt of the tertiary amine and the solvent are removed from the reaction mixture, and
(4) the mixture of products after optional purification is recovered in a ready-to-use form or its components are separated by vacuum distillation, or if desired the compound of the formula (I) is converted into the respective compound of the formula (II) by heat-treatment, or
(b) when a compound of the formula (I) is to be obtained a mole of an amine of the formula (III), wherein $R^1$ is as defined above and $R^2$ is a $C_{1-6}$ alkyl group, or an acid addition salt thereof is used as starting substance, and is proceeded via the same steps as given in process (a), to yield the respective compound of the formula (I), which optionally is purified.

Another object of the invention is the use of the compounds of the formulae (I) and/or (II), wherein $R^1$ and $R^2$ are as defined above, for the oximation and/or trimethylsilylation of a substrate of the formula (V), $$H-Y-Z=O \qquad (V)$$

wherein
Y is oxygen, nitrogen or a sulphur atom or a carboxylic group,
Z is the skeleton of a substrate, and
H is a silylable polar hydrogen.
The compounds of the formula (V), $$(CH_3)_3Si-Y-Z=N-OR^1 \qquad (VI)$$

wherein
$R^1$ is a $C_{1-6}$ alkyl or an aralkyl group,
Y is oxygen, nitrogen or a sulphur atom or a carboxylic group,
Z is the skeleton of the substrate,
said compounds being formed in the oximation and/or trimethylsilylation procedure are also within the scope of the invention.

Still another object of the invention is the use of the compounds of the formula (VI), wherein $R^1$, Y and Z are as defined above, as reference compounds for chromatography.

The compounds of the formulae (I) and/or (II) can be prepared from known starting substances (R. T. Majer, R. J. Hedrick: J.Org.Chem. 30 1270 (1965)) in the following manner: An amine of the formula (III), or an acid addition salt thereof, preferably a hydrochloride salt, is dissolved or suspended in a mixture of an organic solvent and a tertiary amine of sufficient basicity, e.g. a tri-(lower alkyl)amine under vigorous stirring.

The organic solvent should be applied in such an amount that a mixture easy-to-stir during the full course of the reaction is obtained. The preferred amount of the solvent is 1 to 5 parts by weight based on the weight of the starting substance, however, in certain cases solvent amounts out of these limits may also be used. The solvent selected for purposes of reaction medium should meet the following requirements: Firstly, it should at least slightly dissolve the acid addition salts of the amines of the formula (III), secondly, its boiling point should be low enough to make it easily removable by distillation. Examples of such solvents are the aliphatic chlorinated hydrocarbons, such as carbon tetrachloride, chloroform, dichloromethane, dichloroethylene, etc., and the ethers, such as diethyl ether, dibutyl ether, tetrahydrofurane and the like. The most advantageous medium is typically an aprotic, slightly polar organic solvent, most preferably the diethyl ether or tetrahydrofurane.

An essential feature of the invention is that a proton binding agent, i.e. a tertiary amine is applied in the reaction resulting in twice higher total yields compared with previous methods by which other types of silylcarbamate derivatives were prepared. It is preferred to use a tertiary amine of sufficient basicity (i.e. a tertiary amine with $pk_b$ value ranging from 2 to 9, preferably from 2 to 5), said amine forming a salt in the reaction which is almost insoluble in the reaction medium, and thus, easy-to-remove e.g. by filtration. Since the tertiary amines are used at least in slight excess to bind all the acid splitting off in the reaction, the excess thereof should subsequently be removed; therefore tertiary amines with relatively low boiling points are preferred.

Typical examples of such tertiary amines are the tri-($C_{1-6}$alkyl)amines from which triethylamine is the most preferred.

Into the mixture consisting of the starting substance, organic solvent and tertiary amine, carbon dioxide gas is bubbled under vigorous stirring at a temperature ranging from 0° C. to the boiling point of the reaction mixture. When an amine of the formula (III) is used as starting material, it is preferred to carry out the reaction below the ambient temperature. In this case the most preferred temperature range is between 0° C. and 5° C. On the other hand, when the acid addition salt of an amine of the formula (III) is applied, it is preferred to carry out the reaction at elevated temperature, preferably at about the boiling point of the reaction mixture.

Introduction of the carbon dioxide is continued until the reaction mixture becomes saturated, i.e. the reaction is complete. When the amine of formula (III) is used in the form of its acid addition salt, the suspension characteristic of the starting reaction mixture is gradually replaced by a fine, powder-like precipitate during the course of the reaction. On the other hand, when the amine, itself, of the formula (III) is used as starting substance, by the end of the reaction there is no precipitate in the reaction mixture.

The N-substituted carbamic acid trialkylammonium salt of the formula (IV) formed in the above reaction may be isolated. It is more preferred, however, to carry out the second step, i.e. the trimethylsilylation without recovering the compound of the formula (IV). Trimethylsilylation is conducted in the same reaction medium as used in the previous step. As trimethylsilylating agents trimethylchlorosilane or hexamethyldisilazane can be used, generaly at a temperature ranging from 0° C. to 5° C. As it is well known, trimethylsilylating agents readily hydrolyze by moisture of air and water content of the solvents, thus dry solvents should be used as reaction medium and atmospheric humidity should be excluded during the reaction. 1 mole of the compound of the formula (IV) can generally be silylated with 1–5 mole, preferably with 1–3 mole of trimethylchlorosilane depending on that whether predominantly compounds of the formula (I) or compounds of the formula (II) are to be prepared. For the preparation of the compounds of the formula (II) about a twice-fold amount of trimethylchlorosilane is needed than for the preparation of the compounds of the formula (I).

Most of the tertiary amine salt formed in the reaction precipitates from the reaction medium and can be removed by conventional techniques, e.g. by filtration. The remaining part of said salt can be precipitated from the reaction mixture by adding an apolar hydrocarbon with a low boiling point to the reaction medium. Typical examples of such hydrocarbons are n-pentane, n-hexane, n-heptane, n-octane, petroleum ether, benzene and the like, from which the n-pentane is the most preferred one. Once the remaining part of the tertiary amine salt precipitated, it can be removed by the above manner. Then the solvent is distilled off, and the residue, consisting substantially of a mixture of N-substituted carbamic acid trimethylsilyl esters of the formulae (I) and (II) comprising 80–95% of the total rough product, can directly be used for trimethylsilylation and/or oxymation. If desired, the compound of the formula (II) can be separated from the mixture by vacuum distillation.

The compounds of the invention can be synthesized also in a one-step way. In this case an amine of the formula (III) or an acid addition salt thereof is added to the mixture of the solvent, tertiary amine and silylating agent and the carbon dioxide is introduced into the mixture.

In process variant (a) of the invention the ratio of the compounds of the formulae (I) and (II) formed in the reaction can be influenced by altering the amounts of the tertiary amine and the silylating agent used in the procedure. More particularly, when the amounts of the reactants are increased compared to the amount of the amine of the formula (III) or an acid addition salt thereof, the ratio of the resulting compound of the formula (II) is increased in the product-mixture.

Process variant (b) is applicable when a compound of the formula (I) is to be obtained, wherein $R^2$ is a $C_{1-6}$ alkyl group and $R^1$ is as defined above. In this case an amine of the formula (III), wherein $R^2$ is a $C_{1-6}$ alkyl group and $R^1$ is as defined above, or an acid addition salt thereof is applied as starting material.

The invention is elucidated in detail by the aid of the following non-limiting Examples.

EXAMPLE 1

(a) In a 1000 ml round bottom flask equipped with a stirrer, a reflux condenser, a dropping funnel, a gas inlet and gas outlet, a suspension of 42 g (0.5 mole) of methoxyamine hydrochloride and 151.5 g (1.5 mole) of triethylamine in 250 ml dry diethyl ether is prepared. Into this suspension dry carbon dioxide gas is introduced under external ice cooling and vigorous stirring causing the formation of a powder-like precipitate characteristic of the triethylammonium salt of N-methoxycarbamic acid. Introduction of the carbon dioxide is maintained until the gas uptake has been terminated (about 5 hrs) showing that the reaction is substantially complete. Then 108.5 g (1 mole) of trimethylchlorosilane is added under continuous carbon dioxide introduction, stirring and ice cooling over about 1.5 hrs. The reaction mixture is stirred for additional two hours under cooling and then is left to warm up to room temperature. The precipitated triethylamine hydrochloride is filtered off and from the filtrate the ether is removed by distillation. To the residue 100 ml n-pentane is added causing the precipitation of the residual amount of triethylamine hydrochloride, which, again, is removed by filtration. From the filtrate the n-pentane is distilled off under reduced pressure, and the residue is purified by vacuum distillation. The rough product so obtained consists substantially of two principal components comprising 90–92% of the total product. Said main components are N-methoxy,N-trimethylsilylcarbamic acid trimethylsilyl ester and N-methoxycarbamic acid trimethylsilyl ester and the molar ratio thereof is about 2:1. The remaining part of the product contains some residual solvent, triethylamine and hexamethyldisiloxane, thus can directly be applied for most of the practical purposes, e.g. for trimethylsilylation and/or methoxymation without further purification.

Fractional distillation of the product gives 19.5 g (0.12 mole) of N-methoxycarbamic acid trimethylsilyl ester (b.p.: 32–34° C./2.5 mbar) and 58.8 g (0.25 mole) of N-methoxy,N-trimethylsilylcarbamic acid trimethylsilyl ester (b.p.: 55–58° C./2.5mbar). Yields, physical constants as well as spectroscopic and gas chromatographic data are summarized in a table presented after Example 6.

(b) The same procedure is followed as described in Example 1(a), except that the first reaction step is carried out at the boiling point of the reaction mixture. At the end of the two-step process 22.8 g (0.14 mole) of N-methoxycarbamic acid trimethylsilyl ester and 68.2 g (0.29 mole) of N-methoxy,N-trimethylsilycarbamic acid trimethylsilyl ester are obtained with the same physical characteristics as in Example 1a.

(c) 42 g (0.5 mole) of methoxyamine hydrochloride, 250 ml of dry chloroform, 151.5 g (1.5 mole) of triethylamine, 54.2 g (0.5 mole) of trimethylchlorosilane and 80.5 g (0.5 mole) of hexamethyldisilazane are charged into the same apparatus as described in Example 1a. Into this mixture carbon dioxide is introduced at 60–70° C. under stirring. The massive suspension originally present gradually is changed into a loose precipitate. The course of the reaction is monitored by GC analysis showing that after 5 hours the reaction is substantially complete. The reaction mixture is then worked up acording to Example 1a. In the product obtained (80.7 g) the molar ratio of the compound of formula (I) to that of the compound of the formula (II) is about 1:2, and these two components comprise 96% of the rough product, representing a total yield of 73.2%.

EXAMPLE 2

49 g (0.5 mole) of methyl-methoxyamine hydrochloride, 101 g (1 mole) of triethylamine in 250 ml of dry ether is treated with carbon dioxide in the same apparatus and under the same conditions as described in Example 1a. When the carbon dioxide absorption has been ceased, 54 g (0.5 mole) of trimethylchlorosilane is added to the reaction mixture over about 1 hour. Following the same procedure as in Example 1a. 73.2 g (82%) of N-methoxy,N-methylcarbamic acid trimethylsilyl ester are obtained. B.p.: 38–41° C./2.5 mbar.

EXAMPLE 3

24 g (0.5 mole) of methoxyamine and 101 g (1 mole) of triethylamine in 200 ml of dry diethyl ether is treated with carbon dioxide in the same apparatus and under the same conditions as described in Example 1a. When the absorption of the carbon dioxide has been ceased, 108.5 g (1 mole) of trimethylchlorosilane is added to the reaction mixture over 1.5 hours. The reaction mixture is worked up according to Example 1a, yielding a mixture of N-methoxycarbamic acid trimethylsilyl ester and N-methoxy,N-trimethylsilylcarbamic acid trimethylsilyl ester. After vacuum distillation the N-methoxycarbamic acid trimethylsilyl ester with yield of 14.5 g (0.09 mole, 17.8%; b.p.: 32–34° C./2.5 mbar) and the N-methoxy,N-trimethylsilylcarbamic acid trimethylsilyl ester with yield of 72.8 g (0.31 mole, 62%; 55–58° C./2.5 mbar) are obtained.

EXAMPLE 4

(a) 49 g (0.5 mole) of ethoxyamine hydrochloride and 151.5 g (1.5 mole) of triethylamine in 250 ml of dry diethyl ether is treated with carbon dioxide in the same apparatus and same conditions as described in Example 1a. After the carbon dioxide uptake has been finished, 108.5 g (1 mole) of trimethylchlorosilane is added to the reaction mixture over 1.5 hours under vigorous stirring. Following the same procedure as in Example 1a., a mixture of N-ethoxy,N-trimethylsilylcarbamic acid trimethylsilyl ester and N-ethoxycarbamic acid trimethylsilyl ester is obtained. Distillation under reduced pressure give 28.3 g (0.16 mole, 32%; b.p.: 42–45° C./2.5 mbar) of N-ethoxycarbamic acid trimethylsilyl ester and 72.1 g (0.29 mole, 58%; b.p.: 87–91° C./2.5 mbar) of N-ethoxy,N-trimethylsilylcarbamic acid trimethylsilyl ester.

(b) The same procedure is followed as described in Example 4a, except that the first reaction step is carried out at the boiling point of the reaction mixture. At the end of the two-step process 31.5 g (0.18 mole, 36%) of N-ethoxycarbamic acid trimethylsilyl ester and 77.0 g (0.31 mole, 62%) N-ethoxy,N-trimethylsilylcarbamic acid trimethylsilyl ester are obtained with the same physical characteristics as in Example 4a.

EXAMPLE 5

The same procedure is conducted as in Example 3, except that the starting substance is benzyloxyamine. After the two-step reaction the triethylamine hydrochloride is removed by filtration and from the filtrate the solvent and the excess triethylamine is distilled off. The residue contains N-benzyloxy,N-trimethylsilylcarbamic acid trimethylsilyl ester of 92 to 96% purity accompanied by negligible amounts of solvent, triethylamine and traces of hexamethyldisiloxane. The yield is between 45 and 63% and the physical constants are shown in the table presented after Example 6.

EXAMPLE 6

The crude product-mixture of N-methoxycarbamic acid trimethylsilyl ester and N-methoxy,N-trimethylsilylcarbamic acid trimethylsilyl ester obtained according to Example 3, is subjected to heating over several hours, causing the autosilylation of the former into the latter. 70% of N-methoxy,N-trimethylsilyl carbamic acid trimethylsilyl ester is obtained with a boiling poit of 56–58° C./2.5 mbar.

ture. 5 minutes after the initiation of the reaction gas-chromatogramm A, and 25 minutes after the initiation (when the reaction is substantially complete) gas-chromatogramm B both shown by FIG. 1 were obtained.

A JEOL model gas chromatograph equppped with a flame ionization detector and a silanized glass column (2 m×2 mm) packed with 3% by weight of OV-210 on 80–100 mesh Gas Chrom Q was used for analysis. The operating conditions were: oven 262° C., injection block and detector 275° C., nitrogen carrier gas flow rate 20 ml/min.

In FIG. 1 chromatogramm A peak 1. was confirmed for 3-0-trimethylsilylated androsterone-17-methoxime (the desired end-product) and peak 2. for 3-0-trimethylsilylated androsterone (a partially converted intermediate). In FIG. 1, chromatogramm-B only peak 1, characteristic of the desired end-product was detected.

For further identification of the derivative obtained mass spectrometric analysis methods are shown below:

| MS data at 70 eV | | GC retention index on | | |
|---|---|---|---|---|
| (M-X)+ | M/e | OV-210 (262° C.) | and | Se-54 (262° C.) |
| M | 391 | 2915 | | 2735 |
| M-15 | 376 | | | |
| M-31 | 360 | | | |
| M-121 | 270 | | | |

Instead of pyridine other aprotic or dipolar-aprotic solvents such as chloroform or acetonitrile may also be used; in this case the reaction time is somewhat longer. The reaction can be initiated with other acidic catalyst, such as sodium hydrogen sulphate, p-toluenesulphonic

TABLE

Physical and spectroscopic data of the prepared compounds

| No. of Example | $R^1$ | $R^2$ or $(CH_3)_3Si—$ | Yield (%) in terms of the starting compound of formula (III) | b.p. (C.°/mbar) | GC index on OV-1 stationary phase (130° C.) | Mass spectrum M+ m/e | Intensity % | (M-15)+ intensity % | IR (film) (cm$^{-1}$) for νNH | IR (film) (cm$^{-1}$) for νC=O | $^1$H—NMR (CDCl$_3$) peaks for —OSi(CH$_3$)$_3$ and —NSi(CH$_3$)$_3$ (τ) | |
|---|---|---|---|---|---|---|---|---|---|---|---|---|
| 1 and 3 | CH$_3$ | H | 24–30 | 32–34/2.5 | 1012 ± 3 | 163 | 1 | 12 | 3368 | 1694 | 9.68 | — |
| | CH$_3$ | (CH$_3$)$_3$Si— | 50–60 | 55–58/2.5 | 1144 ± 3 | 235 | 31 | 28 | — | 1717 | 9.68 | 9.71 |
| 2 | CH$_3$ | CH$_3$ | 80–90 | 38–41/2.5 | 1058 ± 3 | 177 | 3 | 39 | — | 1692 | 9.68 | — |
| 4 | C$_2$H$_5$ | H | 28–35 | 42–45/2.5 | 1082 ± 3 | 177 | 0.6 | 10 | 3277 | 1693 | 9.67 | — |
| | C$_2$H$_5$ | (CH$_3$)$_3$Si— | 44–60 | 87–91/2.5 | 1189 ± 4 | 249 | 28 | 18 | — | 1715 | 9.67 | 9.72 |
| 5 | C$_6$H$_5$CH$_2$ | (CH$_3$)$_3$Si— | 45–63 | (decomposition) | 1663 ± 5 | 311 | 26 | 17 | — | 1702 | 9.66 | 9.65 |
| 6 | CH$_3$ | (CH$_3$)$_3$Si— | 70 | 55–58/2.5 | 1144 ± 3 | 235 | 31 | 28 | — | 1717 | 9.68 | 9.71 |

EXAMPLE 7

Simultaneous Oximation and Silylation of Androsterone (3β-Hydroxy-5α-Androstan-17-One)

50 mg of androsterone (substrate) measured by an analytic balance is transferred to a 5 ml-volumetric flask and is dissolved in and then made up with pyridine of the analytical grade. A 125 μl aliquot from this stock solution is transferred into a Pierce reaction vessel equipped with a needle-passable rubber cap and then 75 μl (280×10$^{-3}$ mole) of N-methoxy,N-trimethylsilylcarbamic acid trimethylsilyl ester is added. Reaction is initiated by feeding 7.5 μl (66×10$^{-3}$ mole) of trifluoroacetic acid with a Hamilton syringe into the reaction mixture. Derivatisation is running at ambient temperaacid or methanolic solution of HCl.

Besides androsterone the following steroids were subjected to derivatization (in brackets the reactive groups are given):

17α-hydroxyprogesterone (17α-hydroxy; 3,20-dione)
oestrone (3-hydroxy; 17-one)
19-nortestosterone (17β-hydroxy; 3-one)
testosterone (17β-hydroxy; 3-one)
Δ$^1$-methyltestosterone (17α-hydroxy; 3-one)
5-dehydro-epiandrosterone (3β-hydroxy; 17-one)
.˙.progesterone (3,20-dione)
11β-hydroxyprogesterone (11β-hydroxy; 3,20-dione)
oestradiol (3,17β-dihydroxy)
21-hydroxyprogesterone (21-hydroxy; 3,20-dione).

What we claim is:

1. A compound of the formula (I)

$$\begin{array}{c} R^1-O \\ \phantom{R^1-}\diagdown \\ \phantom{R^1-O\diagdown}N-\overset{\overset{\displaystyle O}{\|}}{C}-O-\overset{\overset{\displaystyle CH_3}{|}}{\underset{\underset{\displaystyle CH_3}{|}}{Si}}-CH_3 \\ R^2\phantom{\diagup} \end{array} \quad (I)$$

or a compound of the formula (II)

$$\begin{array}{c} R^1-O \\ \phantom{R^1-}\diagdown \\ \phantom{R^1-O\diagdown}N-\overset{\overset{\displaystyle O}{\|}}{C}-O-\overset{\overset{\displaystyle CH_3}{|}}{\underset{\underset{\displaystyle CH_3}{|}}{Si}}-CH_3 \\ H_3C-\underset{\underset{\displaystyle CH_3}{|}}{Si}-CH_3 \end{array} \quad (II)$$

wherein $R^1$ stands for a $C_{1-6}$ alkyl group of an aralkyl group, and $R^2$ is hydrogen or a $C_{1-6}$ alkyl group.

2. A compound of the Formula (I) defined in claim 1 selected from the group consisting of:
   (a) N-methoxycarbamic acid trimethylsilyl ester;
   (b) N-methoxy,N-methylcarbamic acid trimethylsilyl ester; and
   (c) N-ethoxycarbamic acid trimethylsilyl ester.

3. A compound of the Formula (II) defined in claim 1 selected from the group consisting of:
   (a) N-methoxy,N-trimethylsilylcarbamic acid trimethylsilyl ester;
   (b) N-ethoxy,N-trimethylsilylcarbamic acid trimethylsilyl ester; and
   (c) N-benzyloxy,N-trimethylsilylcarbamic acid trimethylsilyl ester.

4. N-methoxy,N-trimethylsilylcarbamic acid trimethylsilyl ester as defined in claim 1.

* * * * *